US00PP19916P2

(12) United States Plant Patent
Herring et al.

(10) Patent No.: US PP19,916 P2
(45) Date of Patent: Apr. 14, 2009

(54) ***NANDINA DOMESTICA* PLANT NAMED 'AKA'**

(50) Latin Name: *Nandina domestica*
Varietal Denomination: AKA

(75) Inventors: April Herring, Houston, TX (US); Kay Herring, Tomball, TX (US); Adriana Garza, Magnolia, TX (US)

(73) Assignee: TNM Corporation, Magnolia, TX (US)

( * ) Notice: Subject to any disclaimer, the term of this patent is extended or adjusted under 35 U.S.C. 154(b) by 0 days.

(21) Appl. No.: 11/986,339

(22) Filed: Nov. 20, 2007

(51) Int. Cl.
*A01H 5/00* (2006.01)

(52) U.S. Cl. ..... Plt./235
(58) Field of Classification Search ..... Plt./235
See application file for complete search history.

*Primary Examiner*—Annette H Para
*Assistant Examiner*—S. B. McCormick Ewoldt
(74) *Attorney, Agent, or Firm*—Christie, Parker & Hale, LLP.

(57) ABSTRACT

'AKA', a new and distinct variety of *Nandina domestica,* characterized by its upright, compact and dense plant habit; slow growth rate; and unique blush red-colored young foliage and deep green-colored mature foliage. Blush red color of young foliage is retained year-round.

9 Drawing Sheets

Classification: The present invention relates to a new *Nandina domestica* plant.

Variety denomination: The new plant has the varietal denomination 'AKA'.

BACKGROUND OF THE INVENTION

The present Invention relates to a new and distinct cultivar of *Nandina* plant, botanically known as *Nandina domestica,* a member of the Berberidaceae family, commonly known as Heavenly Bamboo.

This new 'AKA' variety resulted from a naturally occurring, whole plant mutation discovered in a cultivated planting of the *Nandina domestica* variety 'Firepower' (not patented). 'AKA' appeared different from 'Firepower' plants growing in 72 cell tray in a greenhouse in Magnolia, Tex. and was initially discovered around November 2004 by the inventors.

The selection of this plant was based on its unique and long-lasting blush red-colored young foliage in contrast to the typical lime green-colored young foliage of the cultivar *Nandina domestica* 'Firepower' (not patented).

The new variety was first reproduced by asexual propagation (micropropagation) at Magnolia Gardens Nursery, Magnolia, Tex. It has since been reproduced numerous times at Magnolia Gardens Nursery, Magnolia, Tex. by asexual propagation (micropropagation). Using this method of asexual propagation it takes 2–3 weeks to initiate root development. Each of the progeny exhibit identical characteristics to the original mutant plant, showing that the unique features of this new *Nandina* are stable and reproduced true to type in successive generations.

SUMMARY OF THE INVENTION

Plants of the new *Nandina* have not been observed under all possible environmental conditions. The phenotype may vary somewhat with variations in environment such as temperature, day length, light intensity, nutrition and water status without, however, any variance in genotype. The following observations and descriptions are of 3-year-old plants grown in 15 gallon containers at Magnolia, Tex., grown in 60% shade in a production nursery with overhead irrigation.

The following traits have been repeatedly observed and are determined to be the unique characteristics of 'AKA'. These characteristics in combination distinguish 'AKA' as a new and distinct cultivar:

1. Upright, compact and dense plant habit.
2. Slow growth rate.
3. Unique blush red colored young foliage and deep green-colored mature foliage. Blush red color of young foliage is retained year-round.

The 'AKA' cultivar has been observed and extensively tested in different growing situations for three years. Its recognizable characteristics, which distinguish it from other known *Nandina* cultivars are: 1. Compact, dense form, with a mature height of 20–24". 2. Slow growth rate. 3. Has proven adaptable to harsh environmental conditions. 4. No flowers or fruit observed to date. 5. Exhibits unique leaf coloration. New growth is blush red. Mature winter foliage is deep red. 6. Is sun and shade tolerant maintaining its proportions equally well in both conditions.

COMPARISON WITH PARENT

The parent cultivar to the new variety is the 'Firepower' variety (not patented), a variety that was developed in New Zealand by New Zealand Nurseries Ltd. Plants of the new *Nandina* may be distinguished from the "Firepower" variety by the following combination of characteristics as seen in side-by-side comparisons conducted in Magnolia, Tex. Plants of the new *Nandina* differed from plants of the cultivar 'Firepower' primarily in developing foliage coloration as plants of the new *Nandina* produced blush red-colored leaves whereas plants of the cultivar 'Firepower' produced lime green-colored leaves. It has also been observed that plants of the new *Nandina* produce a deep red winter colored foliage, Greyed-Red Group 178B, whereas plants of the cultivar 'Firepower' produce a bright red winter colored foliage, Greyed-Red Group 180A.

COMPARISON WITH THE CLOSEST COMMERCIALLY AVAILABLE CULTIVAR

The closest commercially available cultivar to the new variety is the 'Wood's Dwarf' (not patented), a variety that was developed at Oregon State University. Plants of the new *Nandina* differed from plants of the cultivar 'Wood's Dwarf' primarily in developing foliage coloration as plants of the new *Nandina* produced blush red-colored leaves whereas plants of the cultivar 'Wood's Dwarf' produced lime green-colored leaves. It has also been observed that plants of the new *Nandina* are larger as a mature plant at 20–24" tall and 20–24" wide, whereas plants of the cultivar 'Wood's Dwarf' are smaller as a mature plant at 12" tall and 15" wide on average.

BRIEF DESCRIPTION OF ILLUSTRATIONS

FIG. 1-A is a color photograph of the original plant 'AKA' growing in a 15 gallon container in a nursery setting. The original plant has never been pruned and is 22" in height at 3 years of age. Picture taken in the summer.

FIG. 1-B represents the same plants as FIG. 1-A, but as a close-up view.

FIG. 2-A is a side-by-side comparison of the new variety, shown on the right, with a 'Firepower' shown on the left. Both plants are liners in a 72 cell tray.

FIG. 2-B is a side-by-side comparison of the new variety, shown on the right, with a 'Firepower' shown on the left. Both plants are in 1-gallon containers at approximately 8 months of age.

FIG. 3-A is a side-by-side comparison of the new variety's leaf color progression. From left to right is new growth, intermediate growth and mature growth.

FIG. 4-A is a photograph of the new variety at 2 years old growing in a 3 gallon container. This photo shows the unique leaf coloration in the spring.

FIG. 4-B is a photograph of a 3 gallon crop of the new variety propagated by tissue culture at approximately 1 year of age. This photo shows the plant's unique leaf color in the spring and the crop uniformity.

FIG. 5-A is a photograph of the first crops of the new variety in a 72 cell tray propagated by tissue culture showing the uniformity. It also shows the unique color of the new growth. Picture taken in the fall.

FIG. 6-A is a photograph of the new variety's mature winter color.

DETAILED BOTANICAL DESCRIPTION

In the following description, color references are made to The Royal Horticultural Society Colour Chart except where general terms of ordinary dictionary significance is used. The following observations and measurements describe plants grown in a nursery setting in Magnolia, Tex.

Botanical classification: *Nandina domestica* cultivar 'AKA'.

Parentage: A mutation originating in an asexually produced (micropropagated) population of *Nandina domestica* 'Firepower' (not patented).

Propagation:
- *Type.*—By tissue culture or micropropagation.
- *Rooting habit.*—Numerous, fibrous, root initiation seen in 2–3 weeks.

Plant description:
- *Appearance.*—Dwarf, dense, compact mounding form. Slow in growth with a nonspreading habit, and unique foliage coloration.

Mature plant height: 20–24 inches.

Mature plant width: 22–24 inches.

Stems:
- *Stem diameter.*—4–6 mm.
- *Internode length.*—1–2.5 cm.
- *Stem color.*—Young Stems: Closest to Greyed-Orange Group 177C. Mature Stems: Closest to Brown Group 200C.
- *Stem length.*—45–50 cm.
- *Stem form.*—Upright.
- *Stem texture.*—Smooth, longitudinally ridged.
- *Branching habit.*—Branches freely from the basal buds.

Foliage description: Evergreen.
- *Arrangement.*—Alternate, Odd tripinnately Compound.
- *Leaf length.*—36–41 cm.
- *Leaf width.*—38–40 cm.
- *Petiole diameter.*—2–3 mm.
- *Petiole length.*—4–5 cm.
- *Petiole color.*—Petioles on Young Foliage: Greyed-Orange Group 166A. Petioles on Intermediate Foliage: Greyed-Orange Group 177A. Petioles on Mature Foliage: Closest to Yellow-Green Group 144A.
- *Petiolule diameter.*—1 mm on average.
- *Petiolule length.*—2 mm on average.
- *Petiolule color.*—Petiolules on Young Foliage: Greyed-Orange Group 166A. Petiolules on Intermediate Foliage: Greyed-Orange Group 177A. Petiolules on Mature Foliage: Closest to Yellow-Green Group 144C.

Leaflets:
- *Leaflet base.*—Cuneate. Leaflet tips —Acute.
- *Leaflet shape.*—Oblanceolate.
- *Leaflet margin.*—Entire.
- *Leaflet venation pattern.*—Pinnate. Leaflet length.—7–9 cm. Leaflet width.—3–5 cm.
- *Leaflet texture.*—Upper surface: Glaborous. Lower surface: Glaucous.
- *Leaflet aspect.*—Cupped or reflexed.

Color:
- *Young leaflets.*—Upper Side: Closest to Greyed Orange Group 166A. Lower Side: Closest to Greyed Orange Group 165A.
- *Intermediate leaflets.*—Upper Side: Closest to Greyed Orange Group 177A. Lower Side: Closest to Greyed Orange Group 165A.
- *Mature leaflets.*—Upper Side: Closest to Green Group 143. Lower Side: Closest to Green Group 139C.
- *Winter color.*—Greyed-Red Group 178B.
- *Vein color.*—Veins on Young Leaflets: Greyed-Orange Group 166A. Veins on Intermediate Leaflets: Greyed-Orange Group 166A. Veins on Mature Leaflets: Closed to Yellow-Green Group 144B.

Inflorescence: To date, production of inflorescence has not been observed, typical of the variety *Nandina domestica* 'Firepower'.

Seed production: To date, production of berries or seeds has not been observed.

Disease resistance: Resistance to diseases common to plants of *Nandina* has not been observed.

Pest resistance: Resistance to pests common to plants of *Nandina* has not been observed.

We claim:

1. A new and distinct cultivar of *Nandina domestica* plant named 'AKA', as illustrated and described.

* * * * *

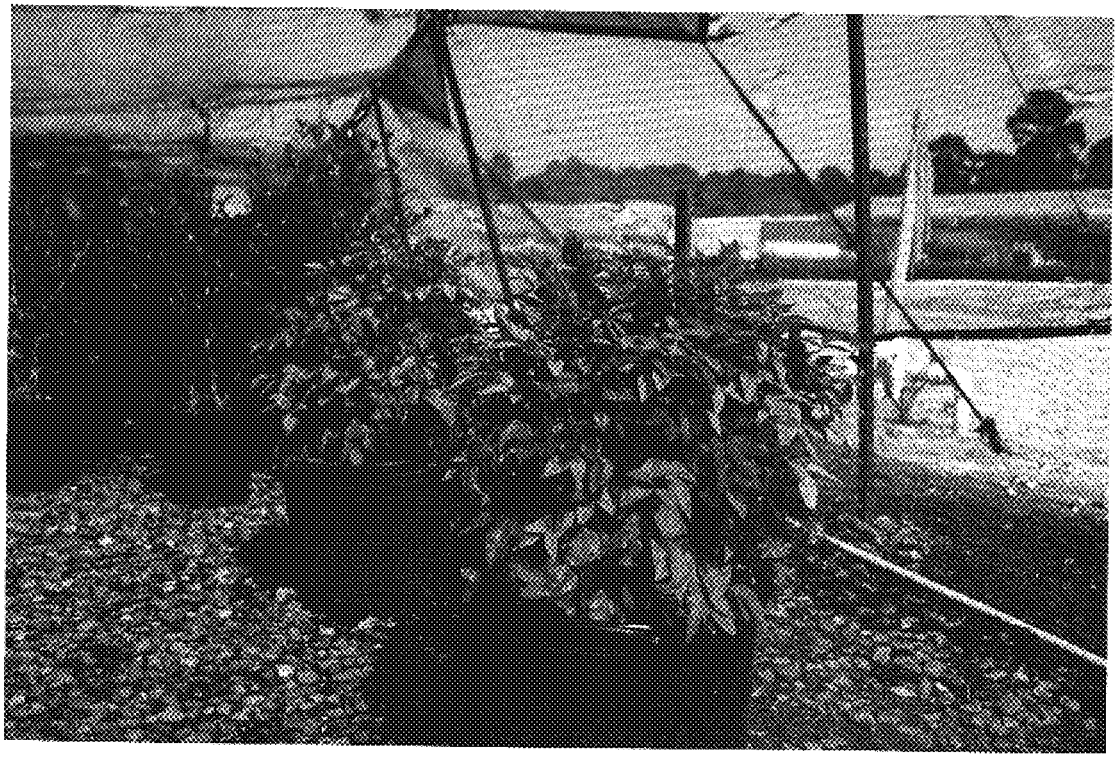
FIG. 1-A

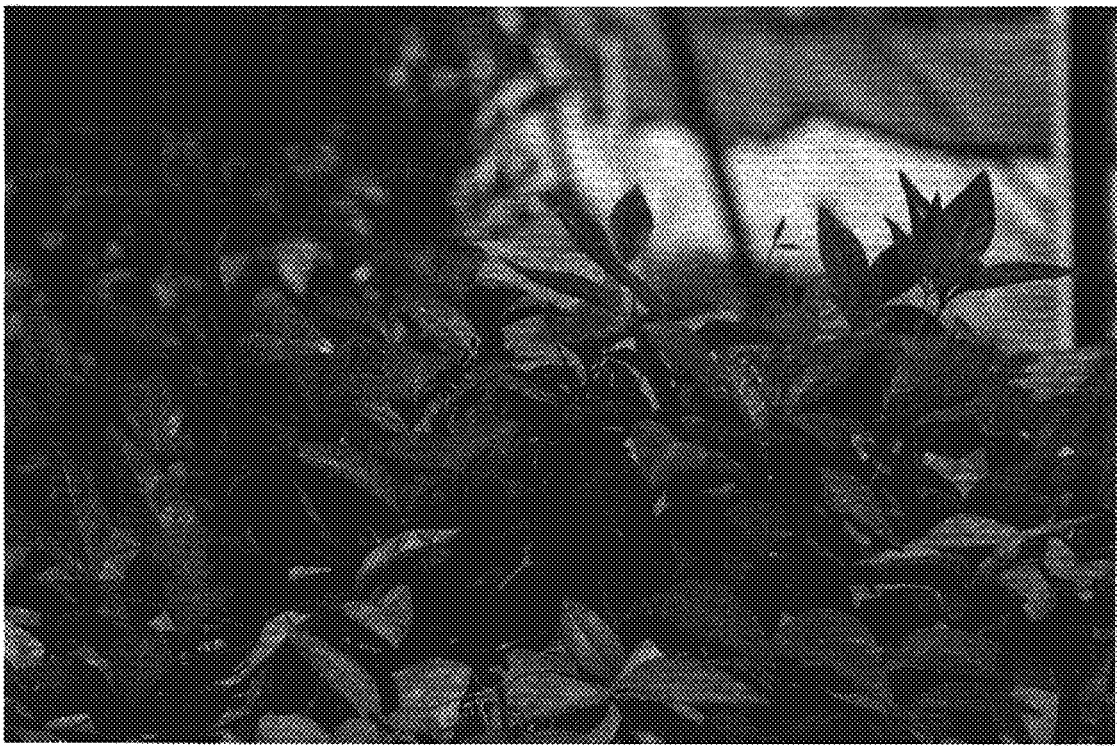
FIG. 1-B

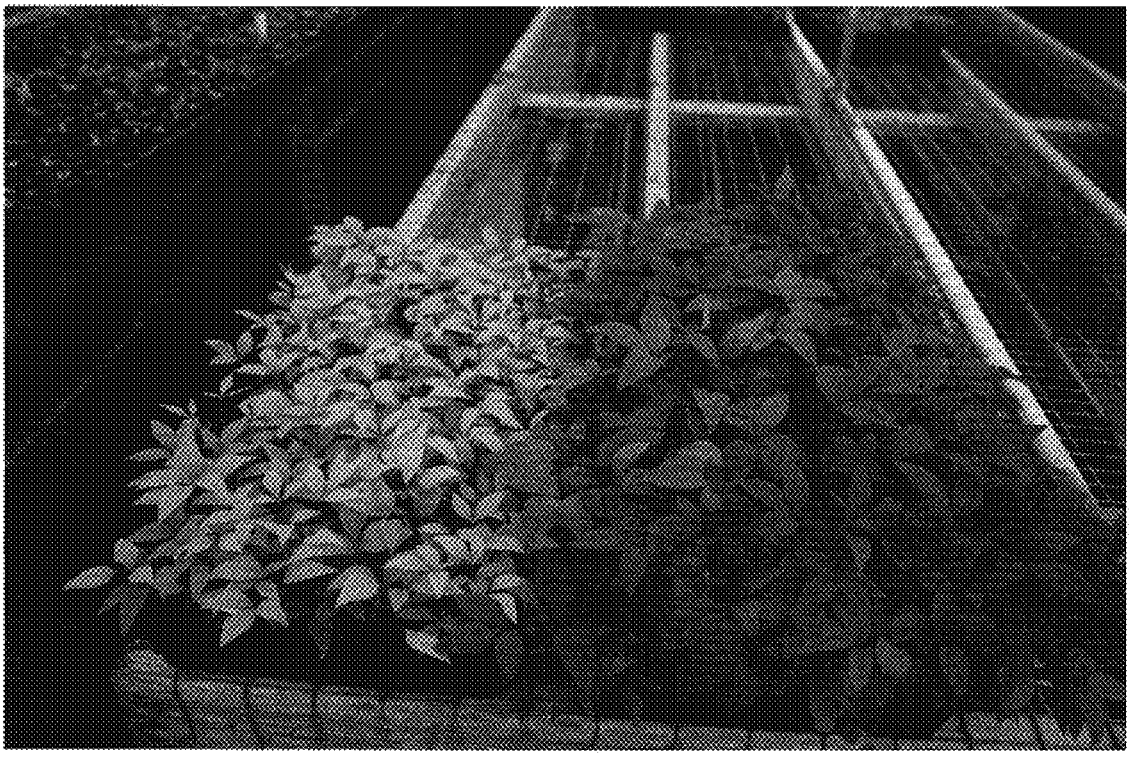
FIG. 2-A

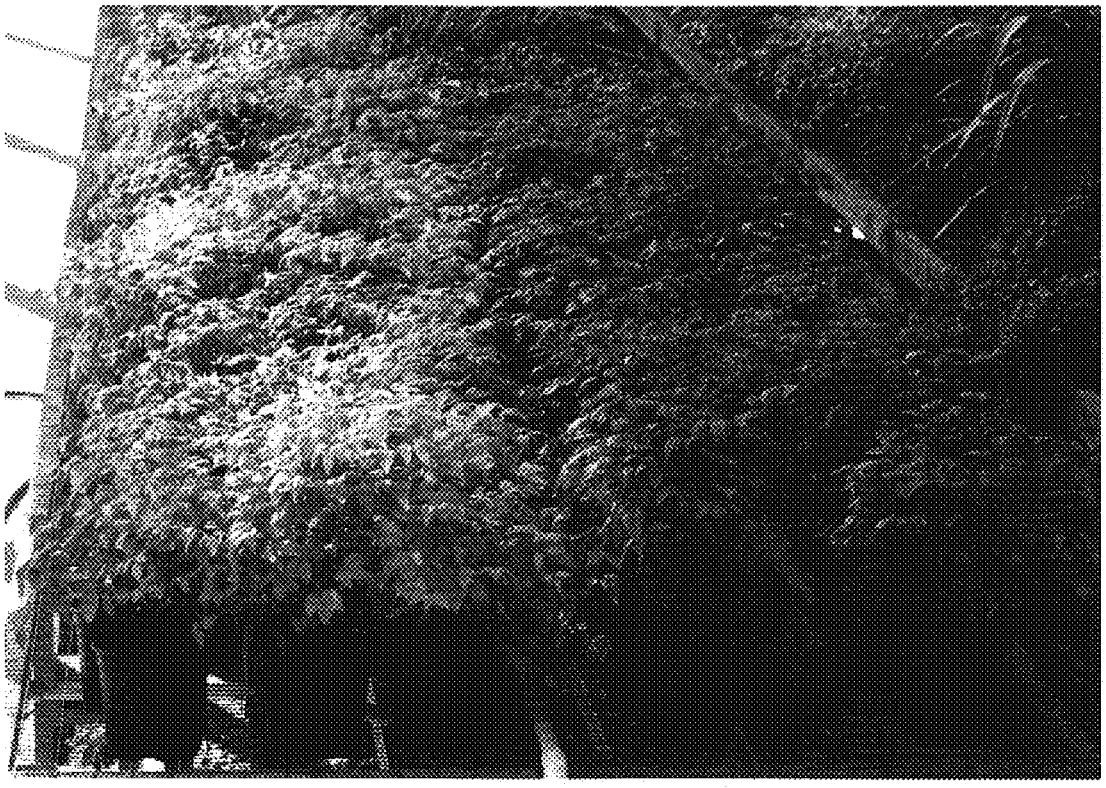
FIG. 2-B

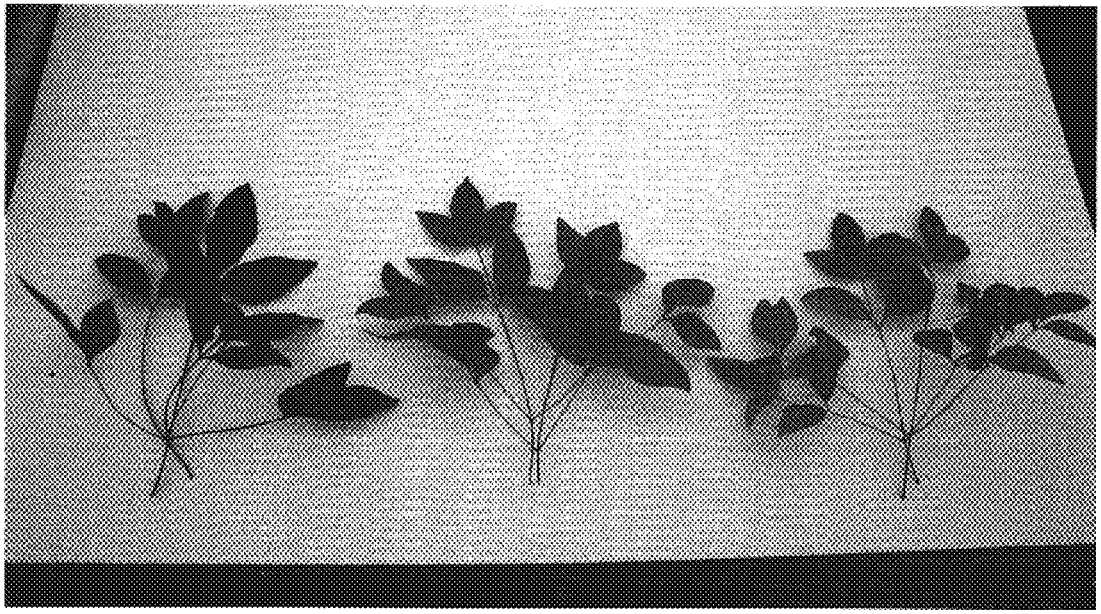
FIG. 3-A

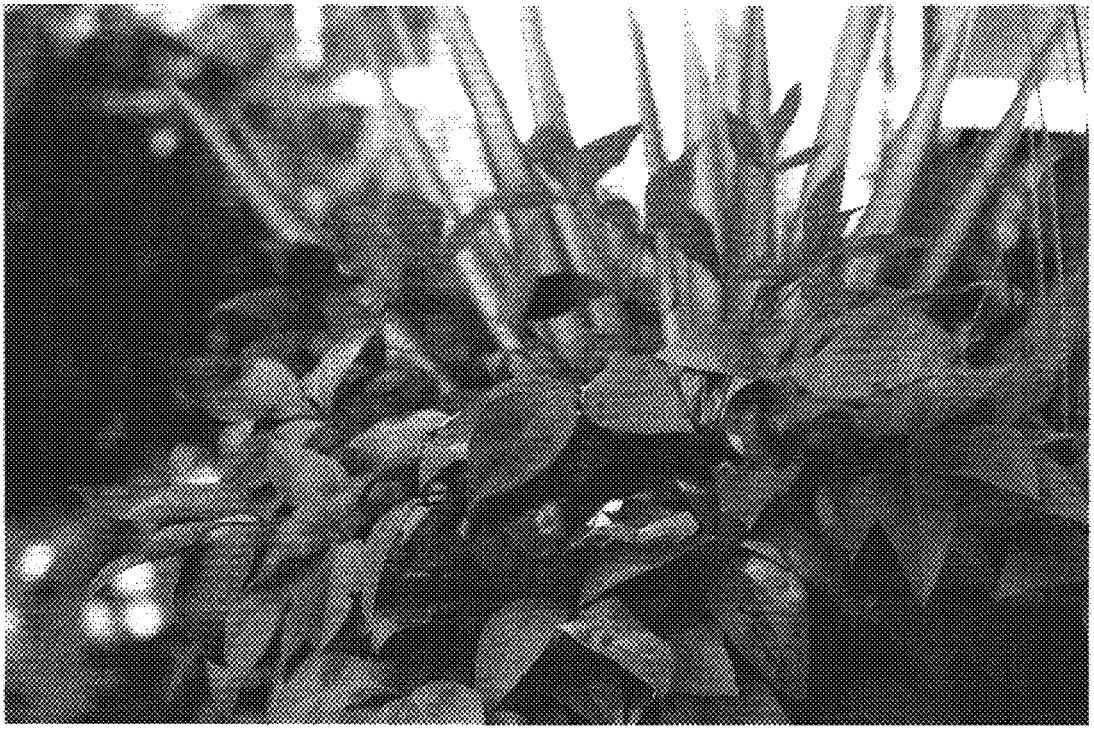
FIG. 4-A

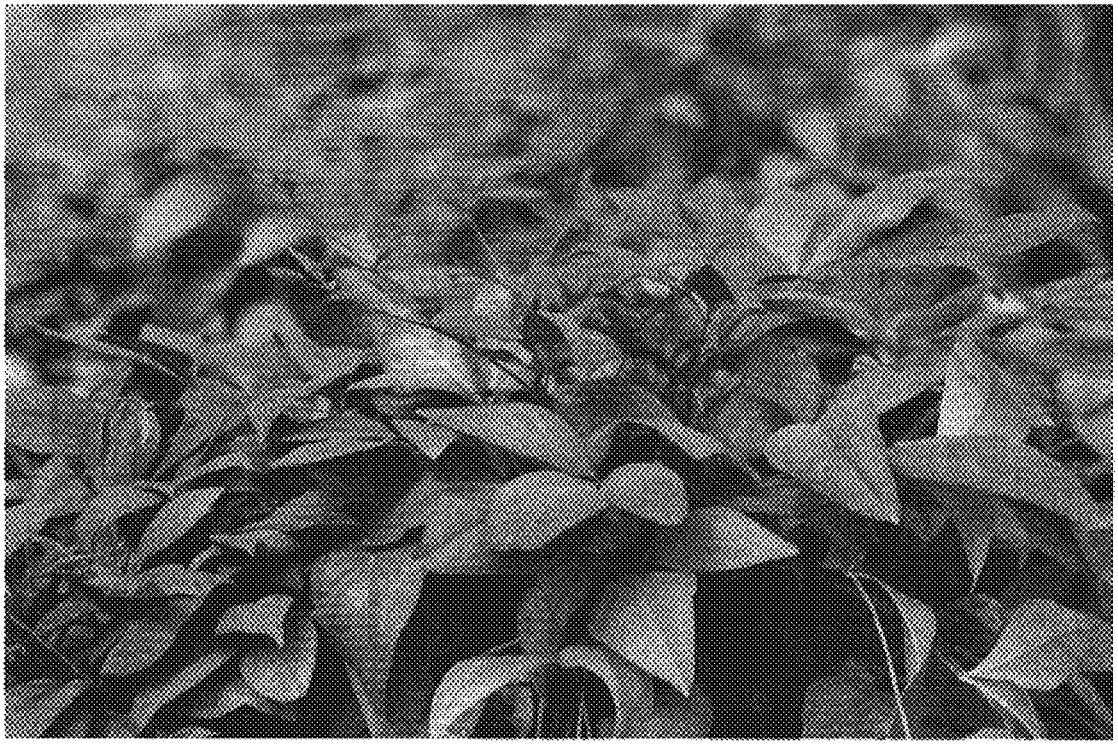
FIG. 4-B

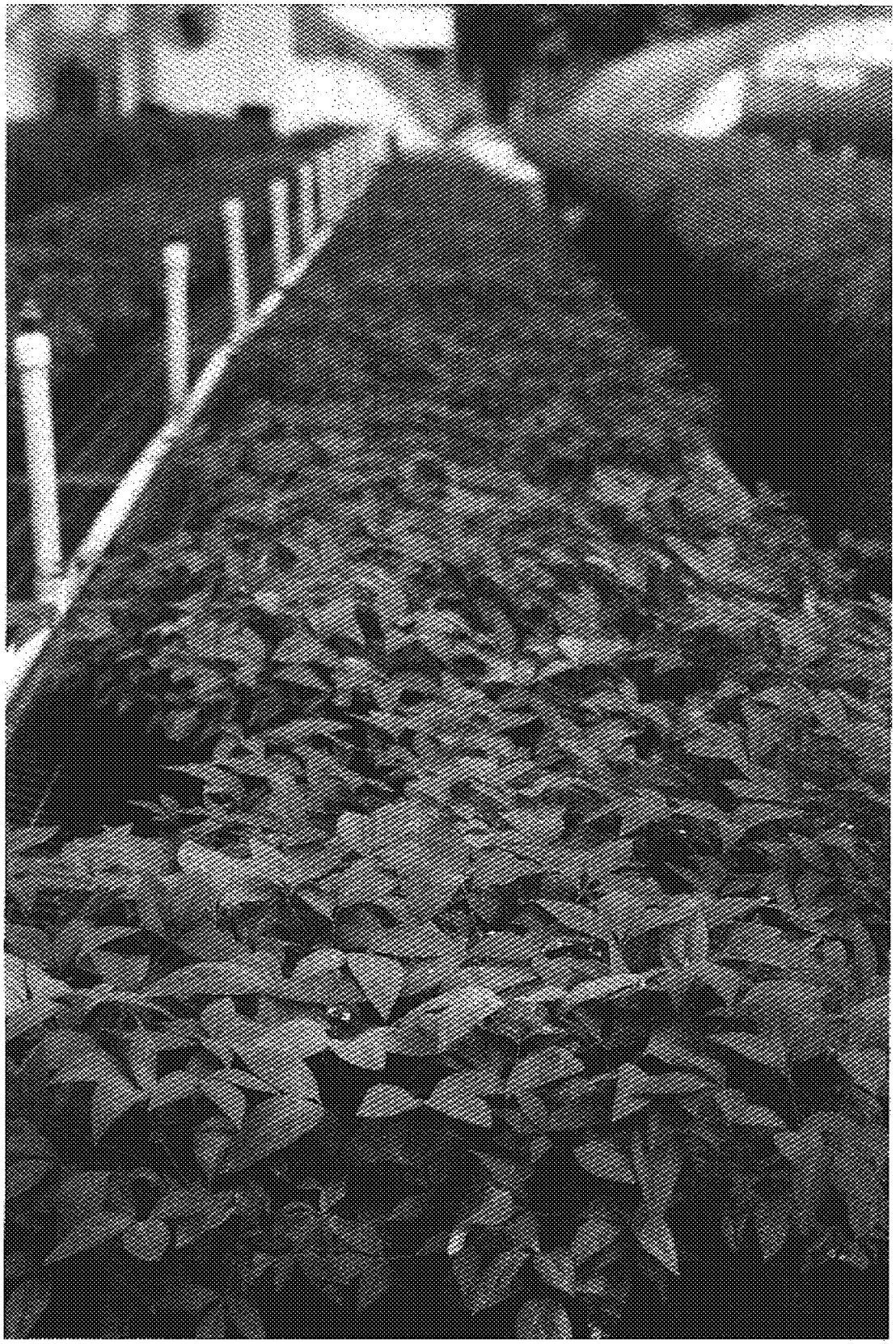
FIG. 5-A

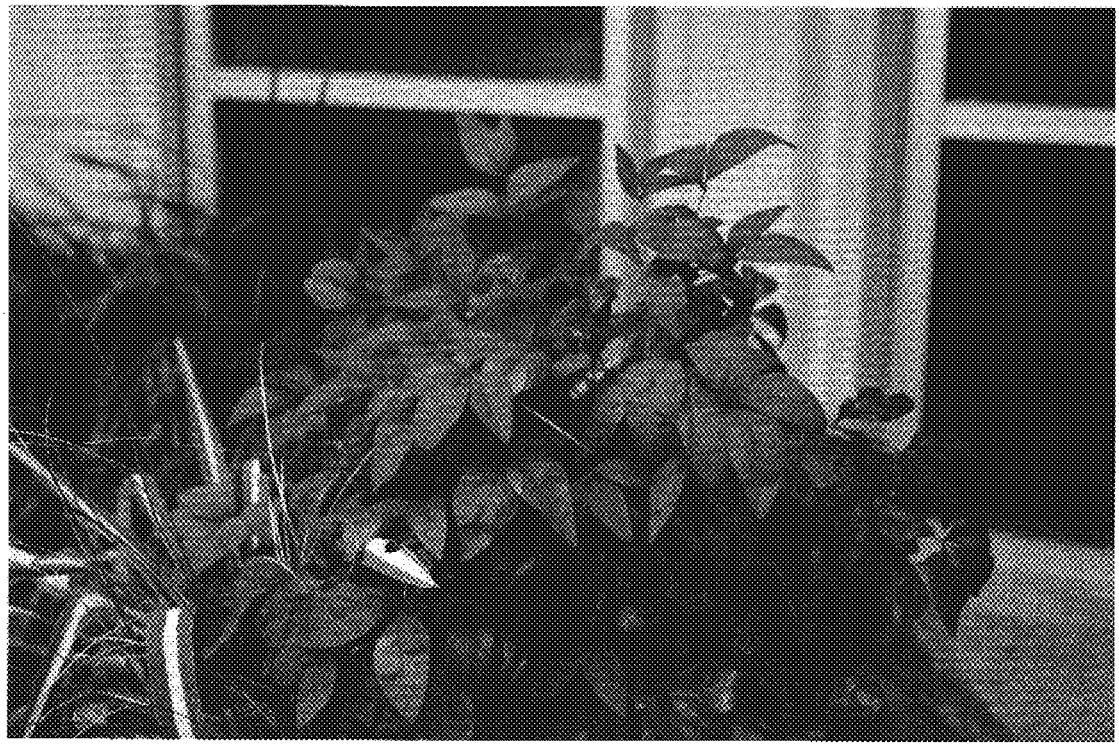
FIG. 6-A'

UNITED STATES PATENT AND TRADEMARK OFFICE

CERTIFICATE OF CORRECTION

PATENT NO. : PP 19,916 P2
APPLICATION NO. : 11/986339
DATED : April 14, 2009
INVENTOR(S) : April S. Herring It is certified that error appears in the above-identified patent and that said Letters Patent is hereby corrected as shown below:

In the Drawings

| | |
|---|---|
| FIG. 4-A, Sheet 6 of 9 | Delete Drawing Sheet 6 and substitute therefore the Drawing Sheet, consisting of Fig. 4-A, as shown on the attached page |
| FIG. 4-B, Sheet 7 of 9 | Delete Drawing Sheet 7 and substitute therefore the Drawing Sheet, consisting of Fig. 4-B, as shown on the attached page |
| FIG. 6-A, Sheet 9 of 9 | Delete Drawing Sheet 9 and substitute therefore the Drawing Sheet, consisting of Fig. 6-A, as shown on the attached page |

Signed and Sealed this

Fourteenth Day of September, 2010

David J. Kappos

David J. Kappos
*Director of the United States Patent and Trademark Office*

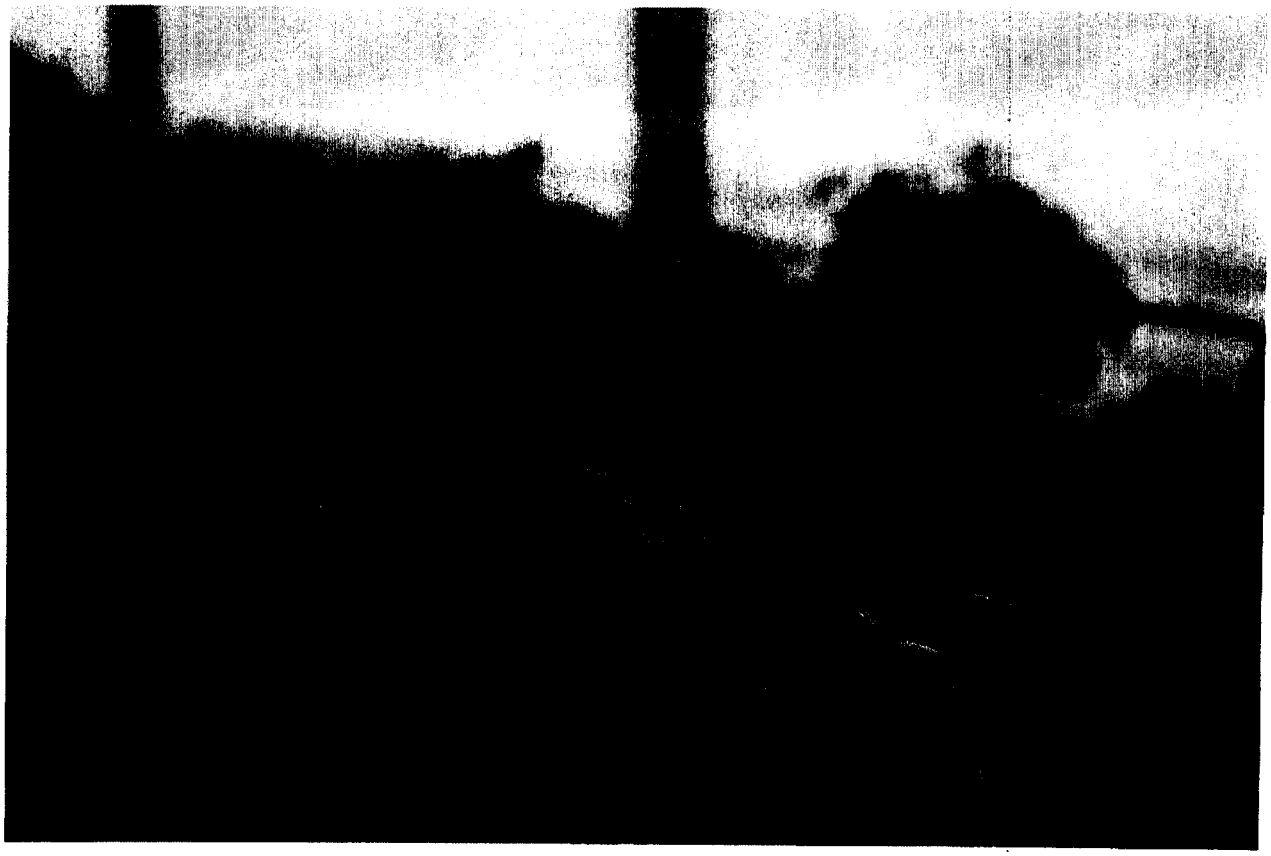
FIG. 4-A

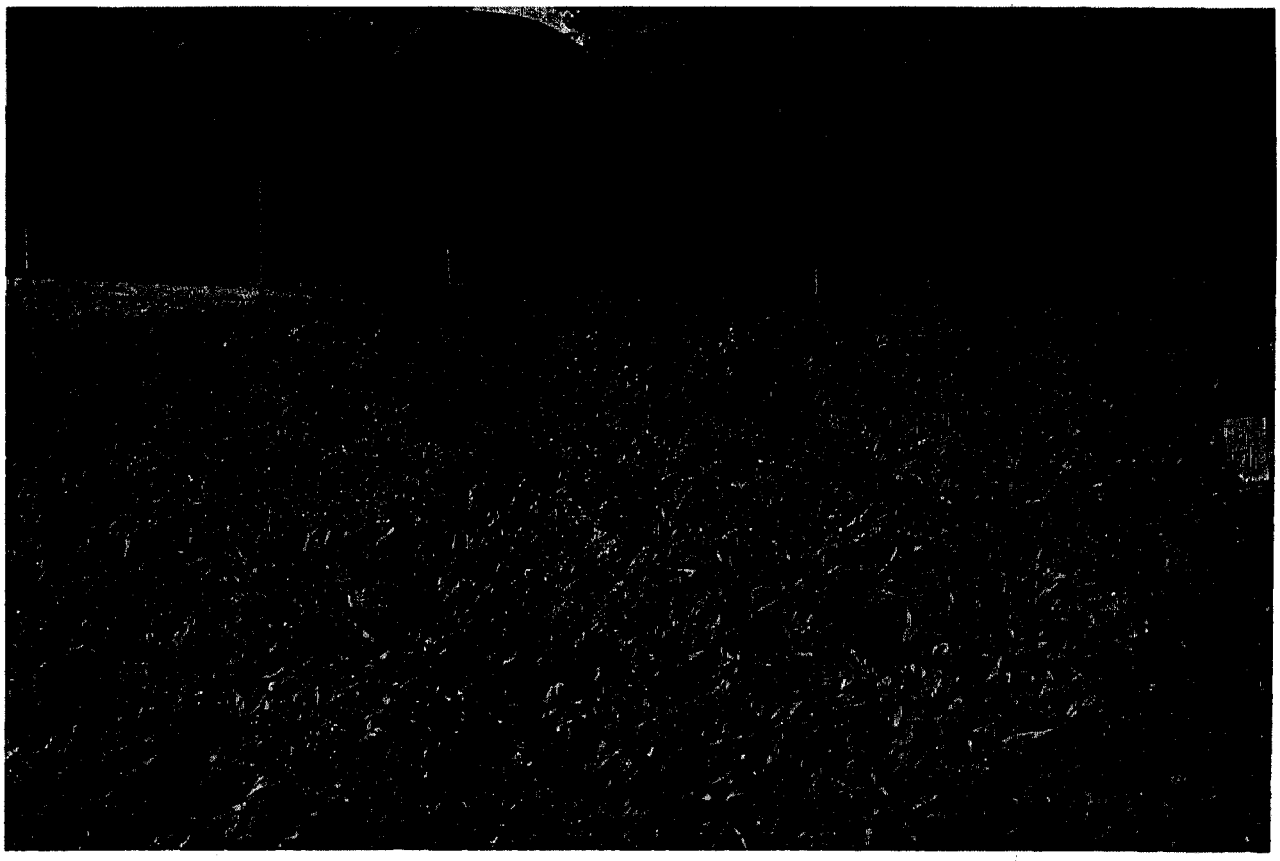
FIG. 4-B

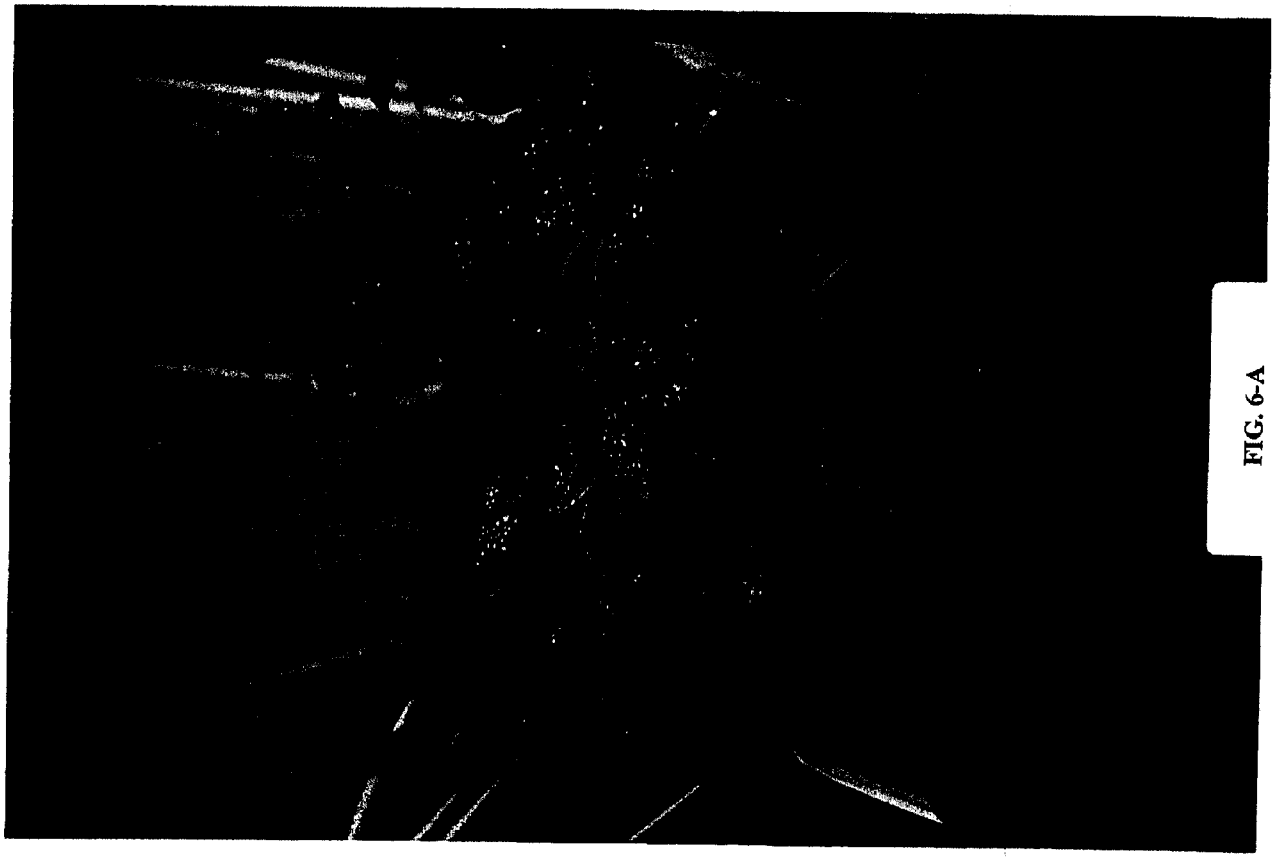
FIG. 6-A